US012178662B2

(12) United States Patent
Miklos et al.

(10) Patent No.: US 12,178,662 B2
(45) Date of Patent: Dec. 31, 2024

(54) CATHETER AND SPRING ELEMENT FOR CONTACT FORCE SENSING

(71) Applicant: Boston Scientific Scimed Inc., Maple Grove, MN (US)

(72) Inventors: Kimberly A. Miklos, Plymouth, MN (US); Joseph Walker, Shoreview, MN (US); Edward J. Maierhofer, Brooklyn Park, MN (US); Garth Mindermann, Bloomington, MN (US); Devon N Arnholt, Shoreview, MN (US); Todd College, Little Canada, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 934 days.

(21) Appl. No.: 15/986,667

(22) Filed: May 22, 2018

(65) Prior Publication Data

US 2018/0338811 A1   Nov. 29, 2018

Related U.S. Application Data

(60) Provisional application No. 62/510,180, filed on May 23, 2017.

(51) Int. Cl.
*A61B 90/00* (2016.01)
*A61B 5/00* (2006.01)
(Continued)

(52) U.S. Cl.
CPC ............ *A61B 90/06* (2016.02); *A61B 5/6852* (2013.01); *A61B 5/6885* (2013.01);
(Continued)

(58) Field of Classification Search
CPC . A61B 5/6852; A61B 5/6885; A61B 18/1492; A61B 90/06; A61B 2090/065; A61M 2025/0002; A61M 25/0054
See application file for complete search history.

(56) References Cited

U.S. PATENT DOCUMENTS 2,515,366 A   7/1950 Zublin
4,328,839 A   5/1982 Lyons et al.
(Continued)

FOREIGN PATENT DOCUMENTS

CN   101978928 A   2/2011
CN   102665586 A   9/2012
(Continued)

OTHER PUBLICATIONS

International Search Report and Written Opinion issued in PCT/US2018/033965, mailed Oct. 23, 2018, 11 pages.

*Primary Examiner* — Daniel W Fowler
*Assistant Examiner* — Braddford C. Blaise
(74) *Attorney, Agent, or Firm* — Nelson Mullins Riley & Scarborough LLP

(57) ABSTRACT

A spring element for a contact force sensing medical catheter. The spring element includes a first ring, a second ring spaced apart from the first ring, a plurality of struts connecting the first ring to the second ring, and a plurality of interlocking features. The second ring and the first ring are coaxially aligned with a longitudinal axis of the spring element. The plurality of struts is configured to permit elastic, relative axial and radial displacement between the first ring and the second ring. The plurality of interlocking features is configured to limit the relative axial and radial displacement between the first ring and the second ring.

18 Claims, 11 Drawing Sheets

(51) Int. Cl.
*A61B 18/00* (2006.01)
*A61B 18/14* (2006.01)
*A61M 25/00* (2006.01)

(52) U.S. Cl.
CPC ........ *A61B 18/1492* (2013.01); *A61B 5/4848* (2013.01); *A61B 2018/00351* (2013.01); *A61B 2018/00577* (2013.01); *A61B 2090/065* (2016.02); *A61B 90/37* (2016.02); *A61B 2090/378* (2016.02); *A61B 2090/3784* (2016.02); *A61B 2218/002* (2013.01); *A61M 2025/0002* (2013.01)

(56) References Cited

U.S. PATENT DOCUMENTS

| | | | |
|---|---|---|---|
| 6,053,922 A | 4/2000 | Krause et al. | |
| 6,273,876 B1* | 8/2001 | Klima | A61M 25/005 604/264 |
| 8,376,865 B2 | 2/2013 | Forster et al. | |
| 2004/0243143 A1* | 12/2004 | Corcoran | A61M 25/0043 606/108 |
| 2005/0080400 A1* | 4/2005 | Corcoran | A61M 25/0054 604/523 |
| 2006/0281566 A1* | 12/2006 | Lee | F16D 3/52 464/149 |
| 2008/0140006 A1* | 6/2008 | Eskuri | A61B 5/6848 604/117 |
| 2008/0294158 A1 | 11/2008 | Pappone et al. | |
| 2010/0152574 A1* | 6/2010 | Erdman | A61M 25/01 600/424 |
| 2011/0130648 A1* | 6/2011 | Beeckler | A61M 25/0054 600/424 |
| 2011/0190664 A1* | 8/2011 | Majercak | A61M 25/00 600/585 |
| 2011/0313417 A1* | 12/2011 | De La Rama | A61B 18/1492 606/41 |
| 2012/0150075 A1* | 6/2012 | Ludwin | A61B 18/1492 600/587 |
| 2012/0303005 A1 | 11/2012 | Forster et al. | |
| 2013/0303886 A1* | 11/2013 | Ludwin | A61B 5/065 600/424 |
| 2014/0336640 A1* | 11/2014 | Beeckler | A61B 18/1492 606/41 |
| 2015/0374252 A1* | 12/2015 | de la Rama | A61B 18/1492 600/374 |
| 2017/0127974 A1* | 5/2017 | Bonyak | A61B 5/062 |
| 2017/0189103 A1* | 7/2017 | Beeckler | A61B 5/061 |
| 2018/0256110 A1* | 9/2018 | Govari | A61B 5/107 |
| 2018/0256247 A1* | 9/2018 | Govari | A61N 1/0563 |

FOREIGN PATENT DOCUMENTS

| | | |
|---|---|---|
| CN | 102892453 A | 1/2013 |
| WO | 2017027419 A1 | 2/2017 |
| WO | 2017027421 A1 | 2/2017 |

\* cited by examiner

CATHETER AND SPRING ELEMENT FOR CONTACT FORCE SENSING

CROSS-REFERENCE TO RELATED APPLICATION

This application claims priority to Provisional Application No. 62/510,180, filed May 23, 2017, which is herein incorporated by reference in its entirety.

TECHNICAL FIELD

The present disclosure relates generally to various force sensing catheter features. More specifically, the disclosure relates to force sensing catheters and spring elements for force sensing catheters.

BACKGROUND

Various cardiac abnormalities can be attributed to improper electrical activity of cardiac tissue. Such improper electrical activity can include, but is not limited to, generation of electrical signals, conduction of electrical signals, and/or mechanical contraction of the tissue in a manner that does not support efficient and/or effective cardiac function. For example, an area of cardiac tissue may become electrically active prematurely or otherwise out of synchrony during the cardiac cycle, thereby causing the cardiac cells of the area and/or adjacent areas to contract out of rhythm. The result is an abnormal cardiac contraction that is not timed for optimal cardiac output. In some cases, an area of cardiac tissue may provide a faulty electrical pathway (e.g., a short circuit) that causes an arrhythmia, such as atrial fibrillation or supraventricular tachycardia. In some cases, inactivate tissue (e.g., scar tissue) may be preferable to malfunctioning cardiac tissue.

Cardiac ablation is a procedure by which cardiac tissue is treated to inactivate the tissue. The tissue targeted for ablation may be associated with improper electrical activity, as described above. Cardiac ablation can lesion the tissue and prevent the tissue from improperly generating or conducting electrical signals. For example, a line, a circle, or other formation of lesioned cardiac tissue can block the propagation of errant electrical signals. In some cases, cardiac ablation is intended to cause the death of cardiac tissue and to have scar tissue reform over the lesion, where the scar tissue is not associated with the improper electrical activity. Lesioning therapies include electrical ablation, radiofrequency ablation, cyroablation, microwave ablation, laser ablation, and surgical ablation, among others. While cardiac ablation therapy is referenced herein as an exemplar, various embodiments of the present disclosure can be directed to ablation of other types of tissue and/or to non-ablation diagnostic and/or catheters that deliver other therapies.

Ideally, an ablation therapy can be delivered in a minimally invasive manner, such as with a catheter introduced to the heart through a vessel, rather than surgically opening the heart for direct access (e.g., as in a maze surgical procedure). For example, a single catheter can be used to perform an electrophysiology study of the inner surfaces of a heart to identify electrical activation patterns. From these patterns, a clinician can identify areas of inappropriate electrical activity and ablate cardiac tissue in a manner to kill or isolate the tissue associated with the inappropriate electrical activation. However, the lack of direct access in a catheter-based procedure may require that the clinician only interact with the cardiac tissue through a single catheter and keep track of all of the information that the catheter collects or is otherwise associated with the procedure. In particular, it can be challenging to determine the location of the therapy element (e.g., the proximity to tissue), the quality of a lesion, and whether the tissue is fully lesioned, under-lesioned (e.g., still capable of generating and/or conducting unwanted electrical signals), or over-lesioned (e.g., burning through or otherwise weakening the cardiac wall). The quality of the lesion can depend on the degree of contact between the ablation element and the targeted tissue. For example, an ablation element that is barely contacting tissue may not be adequately positioned to deliver effective ablation therapy. Conversely, an ablation element that is pressed too hard into tissue may deliver too much ablation energy or cause a perforation.

Other catheter-based therapies and diagnostics can be aided by knowing whether a part of the catheter contacts targeted tissue, and to what degree the part of the catheter presses on the targeted tissue. The tissue exerts a force back on the catheter, which can be measured to assess the contact and the degree to which the catheter presses on the targeted tissue. The accuracy and precision of such force measurements is important for providing consistent, reliable therapy and/or diagnosis.

SUMMARY

Example 1 is a spring element for a contact force sensing medical catheter. The spring element includes a first ring, a second ring spaced apart from the first ring, a plurality of struts connecting the first ring to the second ring, and a plurality of interlocking features. The second ring and the first ring are coaxially aligned with a longitudinal axis of the spring element. The plurality of struts is configured to permit elastic, relative axial and radial displacement between the first ring and the second ring. The plurality of interlocking features is configured to limit the relative axial and radial displacement between the first ring and the second ring.

Example 2 is the spring element of Example 1, wherein each of the plurality of struts extends at least partially in a circumferential direction to permit elastic relative axial and radial displacement between the first ring and the second ring.

Example 3 is the spring element of Example 2, wherein each of the plurality of struts extends at least substantially in the circumferential direction and the plurality of struts are interconnected.

Example 4 is the spring element of Example 2, wherein each of the plurality of struts extends directly between the first ring and the second ring in both the circumferential direction and an axial direction.

Example 5 is the spring element of any of Examples 1-4, wherein the each of the interlocking features extends between the first ring and one of the plurality of struts adjacent to the first ring, between the second ring and one of the plurality of struts adjacent to the second ring, or between two of the plurality of struts adjacent to each other.

Example 6 is the spring element of Example 5, wherein each of the interlocking features includes a tab and an opening. The tab extends from one of the first ring, the second ring, or the one of the plurality of struts. The opening is defined in one of the first ring, the second ring, or another one of the plurality of struts adjacent to the one of the first ring, the second ring, or the one of the plurality of struts from which the tab extends. The opening is configured to engage the tab.

Example 7 is the spring element of Example 6, wherein for at least some of the interlocking features the tab includes a head portion and neck portion connecting the head portion to the one of the first ring, the second ring, or the one of the plurality of struts, the head portion being wider than the neck portion. The opening includes a wide region and a narrow region, wherein the wide region is larger than the head portion of the tab, the narrow region is wider than the neck portion of the tab, and the narrow region is narrower than the head portion of the tab. The head portion of the tab is contained within the wide region and the neck portion of the tab extends through the narrow region such that the opening engages the tab to limit the relative axial and radial displacement between the first ring and the second ring.

Example 8 the spring element of either of Examples 6 or 7, wherein for at least some of the interlocking features, the tab is a first tab and the opening is formed by a second tab and a third tab. The second tab and the third tab are adjacent to each other and extend from one of the first ring, the second ring, or the other one of the plurality of struts adjacent to the one of the first ring, the second ring, or the one of the plurality of struts from which the first tab extends.

Example 9 is the spring element of any of Examples 1-8, wherein the spring element is a one-piece spring element.

Example 10 is a catheter adapted to measure a contact force. The catheter includes a proximal segment, a distal segment, and a spring segment extending from the proximal segment to the distal segment. The spring segment is configured to permit relative displacement between the distal segment and the proximal segment in response to an application of the force on the distal segment. The spring segment includes a spring element according to any of Examples 1-9 and a plurality of sensing elements configured to output a plurality of signals indicative of the relative displacement between the proximal segment and the distal segment.

Example 11 is the catheter of Example 10, wherein the plurality of sensing elements include a plurality of inductive sensors configured to signal a change in inductance caused by changes in the relative displacement between the proximal segment and the distal segment.

Example 12 is the catheter of either of Examples 10 or 11, wherein the proximal segment includes a proximal hub and the distal segment includes a distal hub. The first ring of the spring element is attached to the proximal hub and the second ring of the spring element is attached to the distal hub.

Example 13 is the catheter of Example 12, wherein when the distal segment is in the base orientation with respect to the proximal segment, the proximal and distal hubs are coaxially aligned with the longitudinal axis of the spring element, and when the distal segment is moved out of the base orientation with respect to the proximal segment, the distal hub is no longer coaxially aligned with the longitudinal axis of the spring element.

Example 14 is the catheter of either of Examples 12-13, further including a polymer tube having a lumen and a circumferential surface that defines an exterior of the catheter, wherein each of the proximal hub, the distal hub, and the spring element are at least partially located within the lumen.

Example 15 is the catheter of any of Examples 1-14, wherein the distal segment includes an ablation element configured to deliver ablation therapy.

Example 16 is a spring element for a contact force sensing medical catheter. The spring element includes a first ring, a second ring spaced apart from the first ring, a plurality of struts connecting the first ring to the second ring, and a plurality of interlocking features. The second ring and the first ring are coaxially aligned with a longitudinal axis of the spring element. The plurality of struts is configured to permit elastic, relative axial and radial displacement between the first ring and the second ring. The plurality of interlocking features is configured to limit the relative axial and radial displacement between the first ring and the second ring. The spring element is a one-piece spring element.

Example 17 is the spring element of Example 16, wherein each of the plurality of struts extends at least partially in a circumferential direction to permit elastic relative axial and radial displacement between the first ring and the second ring.

Example 18 is the spring element of Example 17, wherein each of the plurality of struts extends at least substantially in the circumferential direction and the plurality of struts are interconnected.

Example 19 is the spring element of Example 17, wherein each of the plurality of struts extends directly between the first ring and the second ring and in both the circumferential direction and an axial direction.

Example 20 is the spring element of any of Examples 16-19, wherein each of the interlocking features extends between the first ring and one of the plurality of struts adjacent to the first ring, between the second ring and one of the plurality of struts adjacent to the second ring, or between two of the plurality of struts adjacent to each other.

Example 21 is the spring element of Example 20, wherein each of the interlocking features includes at tab and an opening. The tab extends from one of the first ring, the second ring, or the one of the plurality of struts. The opening is defined in one of the first ring, the second ring, or another one of the plurality of struts adjacent to the one of the first ring, the second ring, or the one of the plurality of struts from which the tab extends. The opening is configured to engage the tab.

Example 22 is the spring element of Example 21, wherein for at least some of the interlocking features the tab includes a head portion and neck portion connecting the head portion to the one of the first ring, the second ring, or the one of the plurality of struts, the head portion being wider than the neck portion. The opening includes a wide region and a narrow region, wherein the wide region is larger than the head portion of the tab, the narrow region is wider than the neck portion of the tab, and the narrow region is narrower than the head portion of the tab. The head portion of the tab is contained within the wide region and the neck portion of the tab extends through the narrow region such that the opening engages the tab to limit the relative axial and radial displacement between the first ring and the second ring.

Example 23 is the spring element of Example 21, wherein for at least some of the interlocking features, the tab is a first tab and the opening is formed by a second tab and a third tab. The second tab and the third tab are adjacent to each other and extend from one of the first ring, the second ring, or the other one of the plurality of struts adjacent to the one of the first ring, the second ring, or the one of the plurality of struts from which the first tab extends.

Example 24 is a spring element for a contact force sensing medical catheter. The spring element includes a first ring, a second ring spaced apart from the first ring, a plurality of struts connecting the first ring to the second ring, and a plurality of interlocking features. The second ring and the first ring are coaxially aligned with a longitudinal axis of the spring element. The plurality of struts is configured to permit elastic, relative axial and radial displacement between the first ring and the second ring. The plurality of interlocking features is configured to limit the relative axial and radial displacement between the first ring and the second ring. Each of the interlocking features extends between the first ring and one of the plurality of struts adjacent to the first ring, between the second ring and one of the plurality of struts adjacent to the second ring, or between two of the plurality of struts adjacent to each other. Each of the interlocking features includes a tab and an opening. The tab extends from one of the first ring, the second ring, or the one of the plurality of struts. The opening is defined in one of the first ring, the second ring, or another one of the plurality of struts adjacent to the one of the first ring, the second ring, or the one of the plurality of struts from which the tab extends. The opening is configured to engage the tab.

Example 25 is a catheter adapted to measure a contact force. The catheter includes a proximal segment, a distal segment, and a spring segment extending from the proximal segment to the distal segment. The spring segment is configured to permit relative displacement between the distal segment and the proximal segment in response to an application of the force on the distal segment. The spring segment includes a spring element and a plurality of sensing elements. The spring element includes a first ring, a second ring spaced apart from the first ring, a plurality of struts connecting the first ring to the second ring, and a plurality of interlocking features. The second ring and the first ring are coaxially aligned with a longitudinal axis of the spring element. The plurality of struts is configured to permit elastic, relative axial and radial displacement between the first ring and the second ring. The plurality of interlocking features is configured to limit the relative axial and radial displacement between the first ring and the second ring. The plurality of sensing elements is configured to output a plurality of signals indicative of the relative displacement between the proximal segment and the distal segment.

Example 26 is the catheter of Example 25, wherein each of the plurality of struts extends at least partially in a circumferential direction to permit elastic relative axial and radial displacement between the first ring and the second ring, and the plurality of struts are interconnected.

Example 27 is the catheter of either of Examples 25 or 26, wherein the each of the interlocking features extends between the first ring and one of the plurality of struts adjacent to the first ring, between the second ring and one of the plurality of struts adjacent to the second ring, or between two of the plurality of struts adjacent to each other.

Example 28 is the catheter of 27, wherein each of the interlocking features includes a tab and an opening. The tab extends from one of the first ring, the second ring, or the one of the plurality of struts. The opening is defined in one of the first ring, the second ring, or another one of the plurality of struts adjacent to the one of the first ring, the second ring, or the one of the plurality of struts from which the tab extends. The opening is configured to engage the tab.

Example 29 is the catheter of Example 28, wherein for at least some of the interlocking features the tab includes a head portion and neck portion connecting the head portion to the one of the first ring, the second ring, or the one of the plurality of struts, the head portion being wider than the neck portion. The opening includes a wide region and a narrow region, wherein the wide region is larger than the head portion of the tab, the narrow region is wider than the neck portion of the tab, and the narrow region is narrower than the head portion of the tab. The head portion of the tab is contained within the wide region and the neck portion of the tab extends through the narrow region such that the opening engages the tab to limit the relative axial and radial displacement between the first ring and the second ring.

Example 30 is the catheter of Example 28, wherein for at least some of the interlocking features, the tab is a first tab and the opening is formed by a second tab and a third tab. The second tab and the third tab are adjacent to each other and extend from one of the first ring, the second ring, or the other one of the plurality of struts adjacent to the one of the first ring, the second ring, or the one of the plurality of struts from which the first tab extends.

Example 31 is the catheter of any of Examples 25-30, wherein the spring element is a one-piece spring element.

Example 32 is the catheter of any of Examples 25-31, wherein the plurality of sensing elements include a plurality of inductive sensors configured to signal a change in inductance caused by changes in the relative displacement between the proximal segment and the distal segment.

Example 33 is the catheter of any of Examples 25-32, wherein the proximal segment includes a proximal hub and the distal segment includes a distal hub. The first ring of the spring element is attached to the proximal hub and the second ring of the spring element is attached to the distal hub.

Example 34 is the catheter of Example 33, wherein when the distal segment is in the base orientation with respect to the proximal segment, the proximal and distal hubs are coaxially aligned with the longitudinal axis of the spring element, and when the distal segment is moved out of the base orientation with respect to the proximal segment, the distal hub is no longer coaxially aligned with the longitudinal axis of the spring element.

Example 35 is the catheter of any of Examples 25-34, wherein the distal segment includes an ablation element configured to deliver ablation therapy.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 6A shows the interlocking feature when the spring element is not stressed. FIG. 6B shows the interlocking feature when the spring element is under compressive stress. FIG. 6C shows the interlocking feature when the spring element is under tensile stress.

Figure 1A:
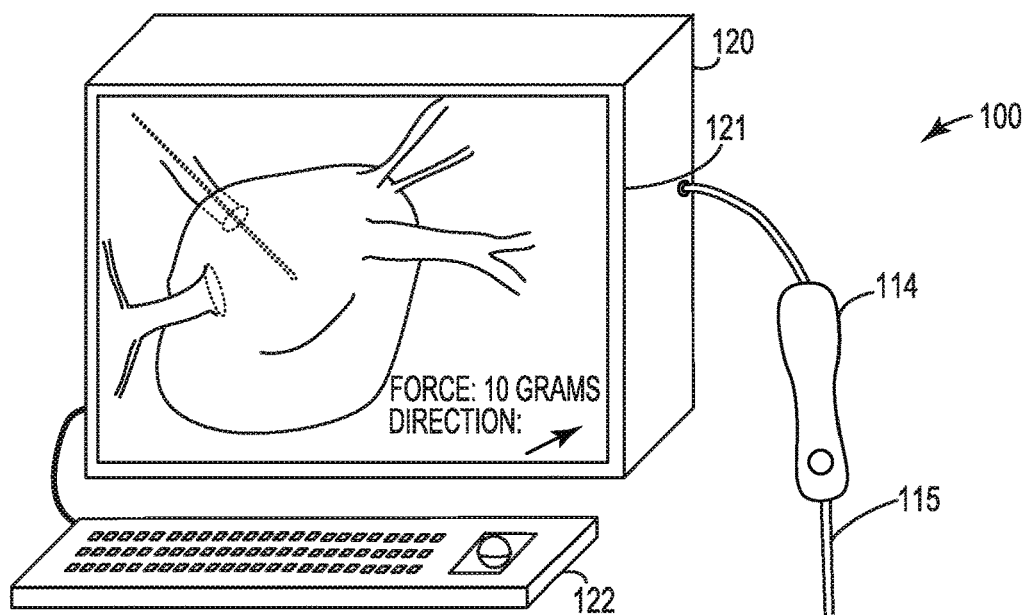
FIGS. 1A-1C show a system for measuring a force with a catheter in accordance with various embodiments of this disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The present disclosure concerns, among other things, methods, devices, and systems for assessing a degree of contact between a part of a catheter (e.g., an ablation element) and tissue. Knowing the degree of contact, such as the magnitude and the direction of a force generated by contact between the catheter and the tissue, can be useful in determining the degree of lesioning of the targeted tissue. Information regarding the degree of lesioning of cardiac tissue can be used to determine whether the tissue should be further lesioned or whether the tissue was successfully ablated, among other things. Additionally or alternatively, an indicator of contact can be useful when navigating the catheter because a user may not feel a force being exerted on the catheter from tissue as the catheter is advanced within a patient, thereby causing vascular or cardiac tissue damage or perforation.

As noted above, the accuracy and precision of such force measurements is important for providing consistent, reliable therapy and/or diagnosis. Force sensing catheters may be provided in a calibrated state so that when used, accurate force measurements are obtained. However, during handling of the force sensing catheter before insertion into the patient, or even under some conditions within the patient, a distal tip of the catheter may be inadvertently subjected to a force sufficient to plastically deform an elastic element, such as a spring element, within the catheter. Plastically deforming the spring element may change the calibration of the catheter such that force sensing measurements from the catheter may no longer be accurate.

Embodiments of the present disclosure include spring elements having interlocking features. The interlocking features can protect the spring element from plastic deformation while experiencing tensile and compressive forces that might otherwise be sufficient to plastically deform the spring element. The interlocking features may not interfere with the operation of the spring element throughout an allowed range of tensile and compressive forces that elastically deform the spring element. Force sensing catheters with spring elements according to embodiments of this disclosure may retain their accuracy after experiencing higher forces than catheters with prior art spring elements.

Figure 1B:
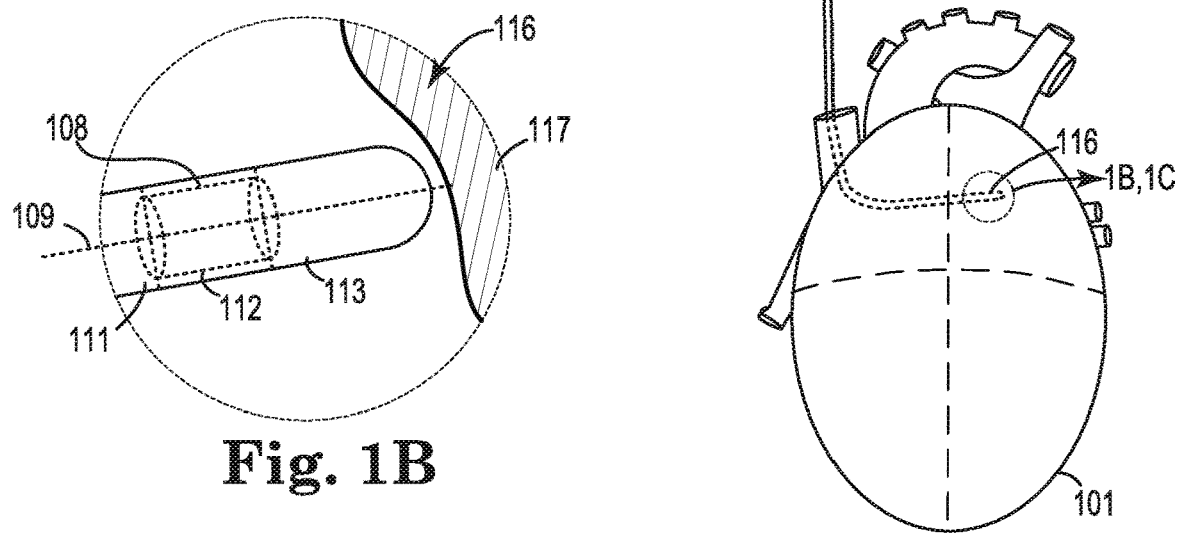
Figure 1C:
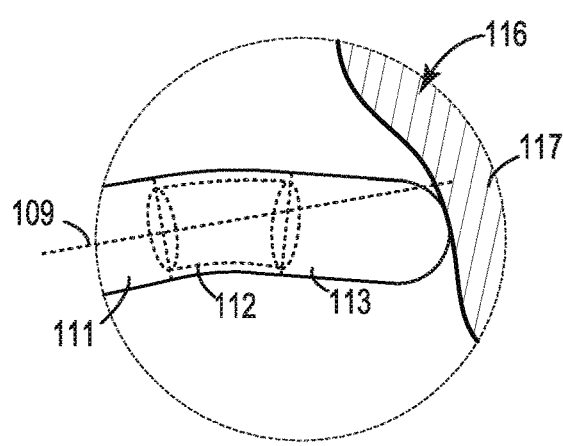

FIGS. 1A-1C illustrate an embodiment of a system 100 for sensing data from inside the body and/or delivering therapy. For example, the system 100 can be configured to map cardiac tissue and/or ablate the cardiac tissue, among other options. The system 100 includes a catheter 110 connected to a control unit 120 via handle 114. The catheter 110 can comprise an elongated tubular member having a proximal end 115 connected with the handle 114 and a distal end 116 configured to be introduced within a heart 101 or other area of the body. As shown in FIG. 1A, the distal end 116 of the catheter 110 is within the left atrium.

As shown in FIG. 1B, the distal end 116 of the catheter 110 includes a proximal segment 111, a spring segment 112, and a distal segment 113. The proximal segment 111, the spring segment 112, and the distal segment 113 can be coaxially aligned with each other in a base orientation as shown in FIG. 1B. Specifically, each of the proximal segment 111, the spring segment 112, and the distal segment 113 are coaxially aligned with a common longitudinal axis 109. The longitudinal axis 109 can extend through the radial center of each of the proximal segment 111, the spring segment 112, and the distal segment 113, and can extend through the radial center of the distal end 116 as a whole. The proximal segment 111, the spring segment 112, and the distal segment 113 can be mechanically biased to assume the base orientation. In some embodiments, the coaxial alignment of the proximal segment 111 with the distal segment 113 can correspond to the base orientation. As shown, the distal end 116, at least along the proximal segment 111, the spring segment 112, and the distal segment 113, extends straight. In some embodiments, this straight arrangement of the proximal segment 111, the spring segment 112, and the distal segment 113 can correspond to the base orientation.

The distal segment 113, or any other segment, can be in the form of an electrode configured for sensing electrical activity, such as electrical cardiac signals. In other embodiments, such an electrode can additionally or alternatively be used to deliver ablative energy to tissue.

The catheter 110 includes force sensing capabilities. For example, as shown in FIGS. 1B and 1C, the catheter 110 is configured to sense a force due to engagement with tissue 117 of heart 101. The distal segment 113 can be relatively rigid while segments proximal of the distal segment 113 can be relatively flexible. In particular, the spring segment 112 may be more flexible than the distal segment 113 and the proximal segment 111 such that when the distal end 116 of the catheter 110 engages tissue 117, the spring segment 112 bends, as shown in FIG. 1C. For example, the distal end 116 of the catheter 110 can be generally straight as shown in FIG. 1B. When the distal segment 113 engages tissue 117, the distal end 116 of the catheter 110 can bend at the spring segment 112 such that the distal segment 113 moves relative to the proximal segment 111. As shown in FIGS. 1B and 1C, the normal force from the tissue moves the distal segment 113 out of coaxial alignment (e.g., with respect to the longitudinal axis 109) with the proximal segment 111 while the spring segment 112 bends. As such, proximal segment 111 and the distal segment 113 may be stiff to not bend due to the force while the spring segment 112 may be less stiff and bend to accommodate the force exerted on the distal end 116 of the catheter 110. One or more sensors within the distal end 116 of the catheter 110 can sense the degree of bending or axial compression of the spring segment 112 to determine the magnitude and the direction of the force, as further discussed herein.

The control unit 120 of the system 100 includes a display 121 (e.g., a liquid crystal display or a cathode ray tube) for displaying information. The control unit 120 further includes a user input 122 which can include one or more buttons, toggles, a track ball, a mouse, touchpad, or the like for receiving user input. The user input 122 can additionally or alternatively be located on the handle 114. The control unit 120 can contain control circuitry for performing the functions referenced herein. Some or all of the control circuitry can alternatively be located within the handle 114.

Figure 2:
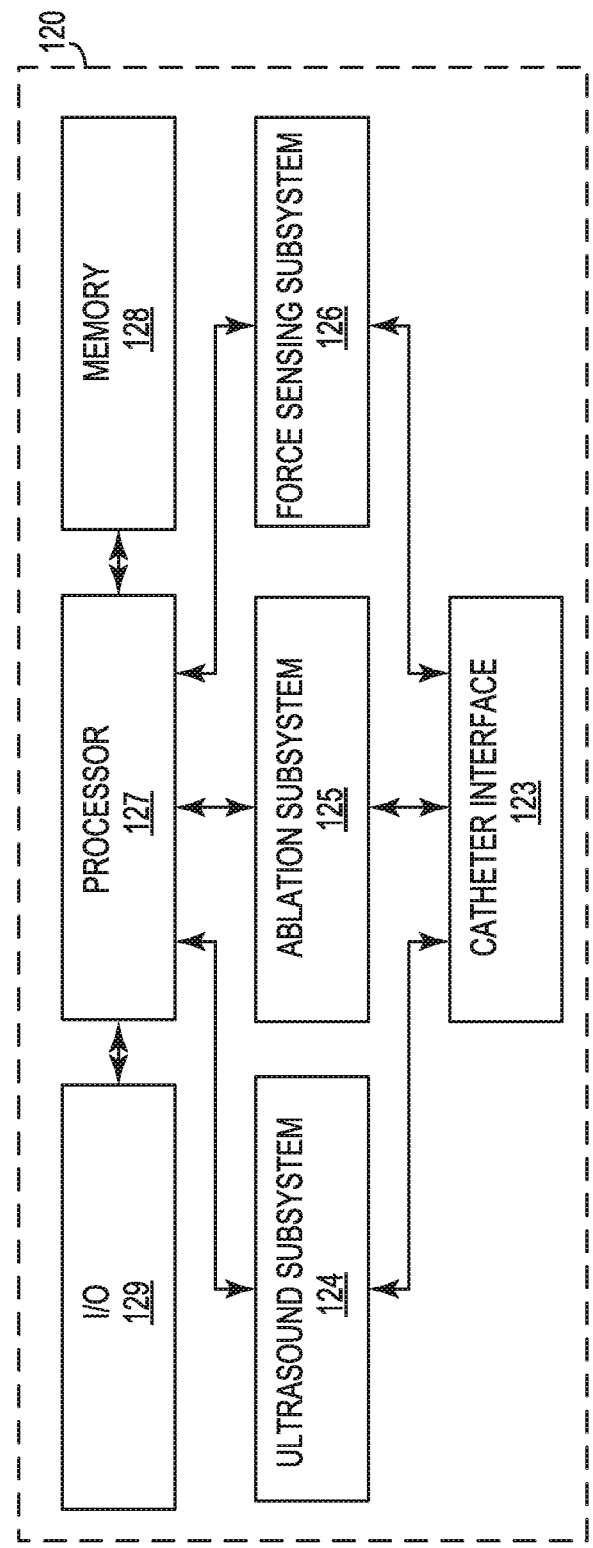
FIG. 2 is a block diagram of circuitry for controlling various functions described herein.

FIG. 2 illustrates a block diagram showing an example of control circuitry which can perform functions referenced herein. This or other control circuitry can be housed within control unit 120, which can comprise a single housing or multiple housings among which components are distributed. Control circuitry can additionally or alternatively be housed within the handle 114. The components of the control unit 120 can be powered by a power supply (not shown), as known in the art, which can supply electrical power to any of the components of the control unit 120 and the system 100. The power supply can plug into an electrical outlet and/or provide power from a battery, among other options.

The control unit 120 can include a catheter interface 123. The catheter interface 123 can include a plug which receives a cord from the handle 114. The catheter 110 can include multiple conductors (not illustrated but known in the art) to convey electrical signals between the distal end 116 and the proximal end 115 and further to the catheter interface 123. It is through the catheter interface 123 that the control unit 120 (and/or the handle 114 if control circuitry is included in the handle 114) can send electrical signals to any element within the catheter 110 and/or receive an electrical signal from any element within the catheter 110. The catheter interface 123 can conduct signals to any of the components of the control unit 120.

The control unit 120 can include an ultrasound subsystem 124 which includes components for operating the ultrasound functions of the system 100. While the illustrated example of control circuitry shown in FIG. 2 includes the ultrasound subsystem 124, it will be understood that not all embodiments may include the ultrasound subsystem 124 or any circuitry for imaging tissue. The ultrasound subsystem 124 can include a signal generator configured to generate a signal for ultrasound transmission and signal processing components (e.g., a high pass filter) configured to filter and process reflected ultrasound signals as received by an ultrasound transducer in a sense mode and conducted to the ultrasound subsystem 124 through a conductor in the catheter 110. The ultrasound subsystem 124 can send signals to elements within the catheter 110 via the catheter interface 123 and/or receive signals from elements within the catheter 110 via the catheter interface 123.

The control unit 120 can include an ablation subsystem 125. The ablation subsystem 125 can include components for operating the ablation functions of the system 100. While the illustrated example of control circuitry shown in FIG. 2 includes the ablation subsystem, it will be understood that not all embodiments may include the ablation subsystem 125 or any circuitry for generating an ablation therapy. The ablation subsystem 125 can include an ablation generator to provide different therapeutic outputs depending on the particular configuration (e.g., a high frequency alternating current signal in the case of radiofrequency ablation to be output through one or more electrodes). The ablation subsystem 125 may support any other type of ablation therapy, such as microwave ablation. The ablation subsystem 125 can deliver signals or other type of ablation energy through the catheter interface 123 to the catheter 110.

The control unit 120 can include a force sensing subsystem 126. The force sensing subsystem 126 can include components for measuring a force experienced by the catheter 110. Such components can include signal processors, analog-to-digital converters, operational amplifiers, comparators, and/or any other circuitry for conditioning and measuring one or more signals. The force sensing subsystem 126 can send signals to elements within the catheter 110 via the catheter interface 123 and/or receive signals from elements within the catheter 110 via the catheter interface 123.

Each of the ultrasound subsystem 124, the ablation subsystem 125, and the force sensing subsystem 126 can send signals to, and receive signals from, the processor 127. The processor 127 can be any type of processor for executing computer functions. For example, the processor 127 can execute program instructions stored within the memory 128 to carry out any function referenced herein, such as determine the magnitude and direction of a force experienced by the catheter 110.

The control unit 120 further includes an input/output subsystem 129 which can support user input and output functionality. For example, the input/output subsystem 129 may support the display 121 to display any information referenced herein, such as a graphic representation of tissue, the catheter 110, and a magnitude and direction of the force experienced by the catheter 110, amongst other options. Input/output subsystem 129 can log key and/or other input entries via the user input 122 and route the entries to other circuitry.

A single processor 127, or multiple processors, can perform the functions of one or more subsystems, and as such the subsystems may share control circuitry. Although different subsystems are presented herein, circuitry may be divided between a greater or lesser numbers of subsystems, which may be housed separately or together. In various embodiments, circuitry is not distributed between subsystems, but rather is provided as a unified computing system. Whether distributed or unified, the components can be electrically connected to coordinate and share resources to carry out functions.

Figure 3:
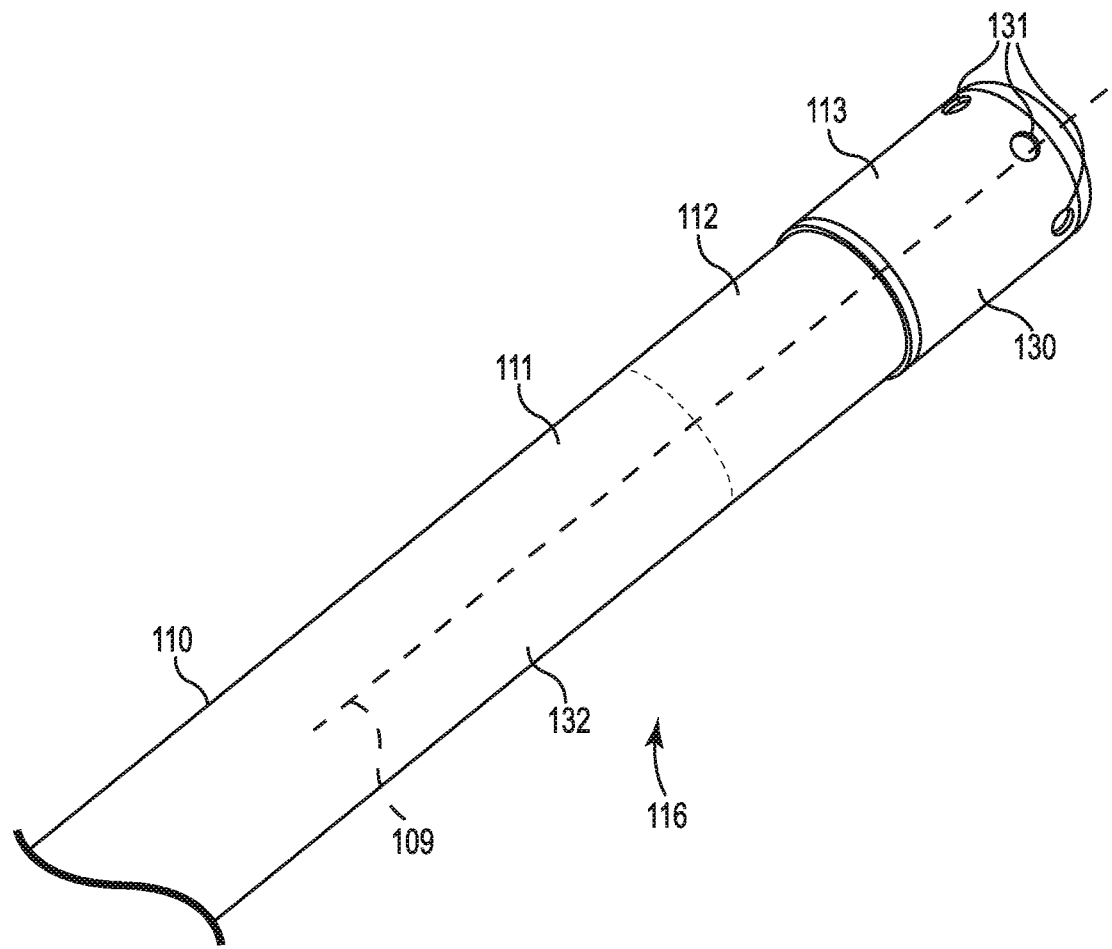
FIG. 3 is a perspective view of a distal end of a catheter in accordance with various embodiments of this disclosure.

FIG. 3 illustrates a detailed view of the distal end 116 of the catheter 110. FIG. 3 shows a catheter shaft 132. The catheter shaft 132 can extend from the distal segment 113 to the handle 114 (FIG. 1A), and thus can define an exterior surface of the catheter 110 along the spring segment 112, the proximal segment 111, and further proximally to the proximal end 115 (FIG. 1A). The catheter shaft 132 can be a tube formed from various polymers, such as polyurethane, polyamide, polyether block amide, silicone, and/or other materials. In some embodiments, the catheter shaft 132 may be relatively flexible, and at least along the spring segment 112 may not provide any material mechanical support to the distal segment 113 (e.g., facilitated by thinning of the wall of the catheter shaft 132 along the spring segment 112).

As shown, the proximal segment 111 can be proximal and adjacent to the spring segment 112. The length of the proximal segment 111 can vary between different embodiments, and can be five millimeters to five centimeters, although different lengths are also possible. The length of the spring segment 112 can also vary between different embodiments and is dependent on the length of underlying features as will be further discussed herein. The spring segment 112 is adjacent to the distal segment 113. As shown in FIG. 3, the distal segment 113 can be defined by an electrode 130. The electrode 130 can be an ablation electrode. In some other embodiments, the distal segment 113 may not be an electrode. The electrode 130 can be in a shell form which can contain other components. The electrode 130 can include a plurality of ports 131. In some embodiments, the ports 131 may be fluidly connected to a source of irrigation fluid for flushing the volume adjacent to the distal segment 113. In some embodiments, one or more ultrasonic transducers, housed within the electrode 130, can transmit and receive signals through the ports 131 or through additional dedicated holes in the tip shell. Additionally or in place of the transducers, one or more miniature electrodes may be incorporated into the electrode 130.

Figure 4:
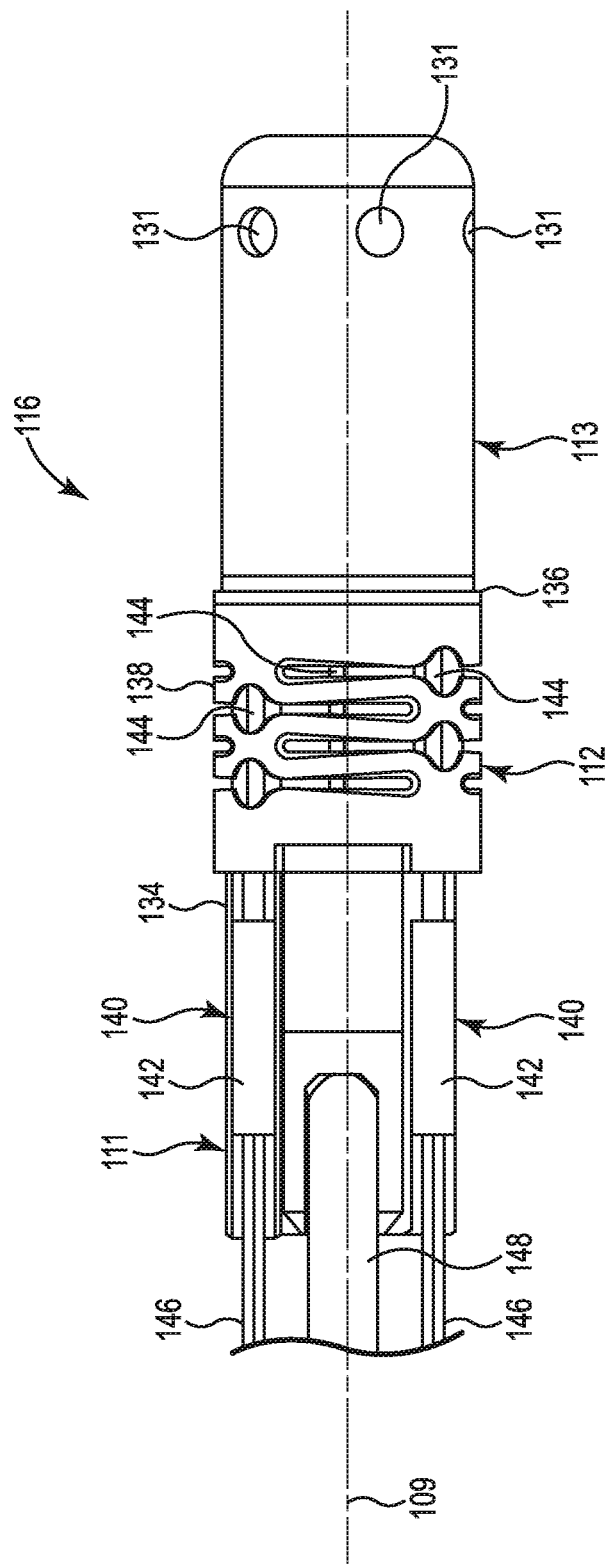
FIG. 4 is a side view of the inside of a distal end of a catheter in accordance with various embodiments of this disclosure.

FIG. 4 shows a side view of the inside of the distal end 116 of the catheter 110 of FIG. 3 after the removal of the catheter shaft 132 to expose various components that underlie the catheter shaft 132. As shown in FIG. 4, the proximal segment 111 may include a proximal hub 134, the distal segment 113 may include a distal hub 136, and the spring segment 112 may include a spring element 138. In some embodiments, one or both of the proximal hub 134 and the distal hub 136 can be formed from polymer materials, such as polyethylene, or PEEK. In other embodiments, one or both of the proximal hub 134 and the distal hub 136 can be formed from a metal, such as a stainless steel or MP35N. In still other embodiments, one or both of the proximal hub 134 and the distal hub 136 can be formed from a composite of metal, polymer, and/or other materials. The spring element 138 can be formed from a resilient material, for example, polymer materials, metals (e.g. stainless steel, MP35N), or other materials. In some embodiments, the spring element 138 may be formed from an MP35N hypotube. The spring element 138 may be formed by, for example, laser cutting, mechanical sawing, or precision electrochemical machining (PEM). In some embodiments, such as those described below in reference to FIGS. 5, 7, 9, and 10, the spring element 138 is a one-piece spring element.

The spring element 138 is a resilient cylindrical tubular structure connecting the distal hub 136 to the proximal hub 134. In some embodiments, the spring element 138 is welded to one or both of the proximal hub 134 and the distal hub 136. In some particular embodiments in which the spring element 138 is formed of MP35N, the spring element 138 is easily welded to the proximal hub 134 and the distal hub 136, which can also be made of MP35N or stainless steel. In other embodiments, the spring element 138 is attached to one or both of the proximal hub 134 and the distal hub 136 by an adhesive. Thus, the spring segment 112 can extend from a distal edge of the proximal hub 134 to a proximal edge of the distal hub 136. As such, the proximal hub 134 can be part of, and may even define the length of, the proximal segment 111 (FIG. 1A). Likewise, the distal hub 136 can be part of the distal segment 113. The spring segment 112 can be a relatively flexible portion that is mostly or entirely mechanically supported by the spring element 138. As such, the proximal hub 134 and the distal hub 136 are stiffer than the spring element 138 such that a force directed on the distal segment 113 causes the distal end 116 to bend along the spring element 138 rather than along the distal segment 113 or the proximal segment 111.

As shown in FIG. 4, the distal end 116 may further include a plurality of sensing elements 140. In the embodiment shown in FIG. 4, each of the plurality of sensing elements 140 is an inductive sensor including a wound coil 142, a magnetically permeable core (not shown), a rod 144 and wires 146. The wound coil 142 is attached to the proximal hub 134, but electrically isolated from the proximal hub 134. The magnetically permeable core is connected to a proximal end of the rod 144 and disposed within the wound coil 142. The rod 144 is connected on its distal end to the distal hub 136. In some embodiments, the rod 144 is formed of a magnetically permeable material and the proximal end of the rod 144 itself forms the magnetically permeable core. The wires 146 electrically connect the wound coil 142 with the control unit 120 (FIG. 1A).

In the embodiment of FIG. 4, there are three sensing elements 140 disposed 120 degrees apart around the longitudinal axis 109, with two being visible in FIG. 4. Three sensing elements 140 are necessary to resolve a three dimensional force vector. However, in other embodiments, fewer or more sensing elements 140 may be employed. In addition, although the embodiment of FIG. 4 shows a particular type of inductive sensor, it is understood that other embodiments can include different types of inductive sensors. Further, it is understood that embodiments can include other types of sensors, such as optical sensors or strain gauge sensors, in addition to, or in place of the inductive sensors 140 shown in FIG. 4.

In the base orientation, the proximal hub 134, the distal hub 136, and the spring element 138 can be coaxially aligned with respect to the longitudinal axis 109, as shown in FIG. 4. For example, the longitudinal axis 109 can extend through the respective radial centers of each of the proximal hub 134, the distal hub 136, and the spring element 138. In use, as the normal force from the tissue moves the distal segment 113 out of coaxial alignment (e.g., with respect to the longitudinal axis 109) with the proximal segment 111 (FIG. 1C), the distal end 116 bends along the spring element 138 causing displacement of the distal hub 136 relative to the proximal hub 134. The displacement of the distal hub 136 causes movement in at least one of the three connected rods 144, displacing the corresponding magnetically permeable core within the corresponding wound coil 142, changing an inductance of the wound coil 142 in a linear fashion. The change in inductance is sensed by the force sensing subsystem 126 of the control unit 120 by way of the wires 146. In this way, the plurality of sensing elements 140 are configured to output a plurality of signals indicative of the relative displacement between the proximal segment 111 and the distal segment 113.

In some embodiments, an inner tube (not shown) can extend through the catheter 110 (e.g., from the handle 114, FIG. 1A), through the proximal hub 134, the spring element 138, and the distal hub 136. The inner tube can include one or more lumens within which one or more conductors (not illustrated) can extend from the proximal end 115 (FIG. 1A) to the distal segment 113, such as for connecting with one or more electrical elements (e.g., ultrasound transducer, electrode, strain sensor, or other component). Coolant fluid can additionally or alternatively be routed through the inner tube. In various embodiments, the catheter 110 is open irrigated (e.g., through the plurality of ports 131) to allow the coolant fluid to flow out of the distal segment 113. Various other embodiments concern a non-irrigated catheter 110.

As shown in FIG. 4, a tether 148 can attach to a proximal end of the proximal hub 134. Considering FIGS. 1A and 4, together, the tether 148 can attach to a deflection mechanism within the handle 114 to cause deflection of the distal end 116. A knob, slider, or plunger on a handle 114 may be used to create tension or slack in the tether 148.

Figure 5:
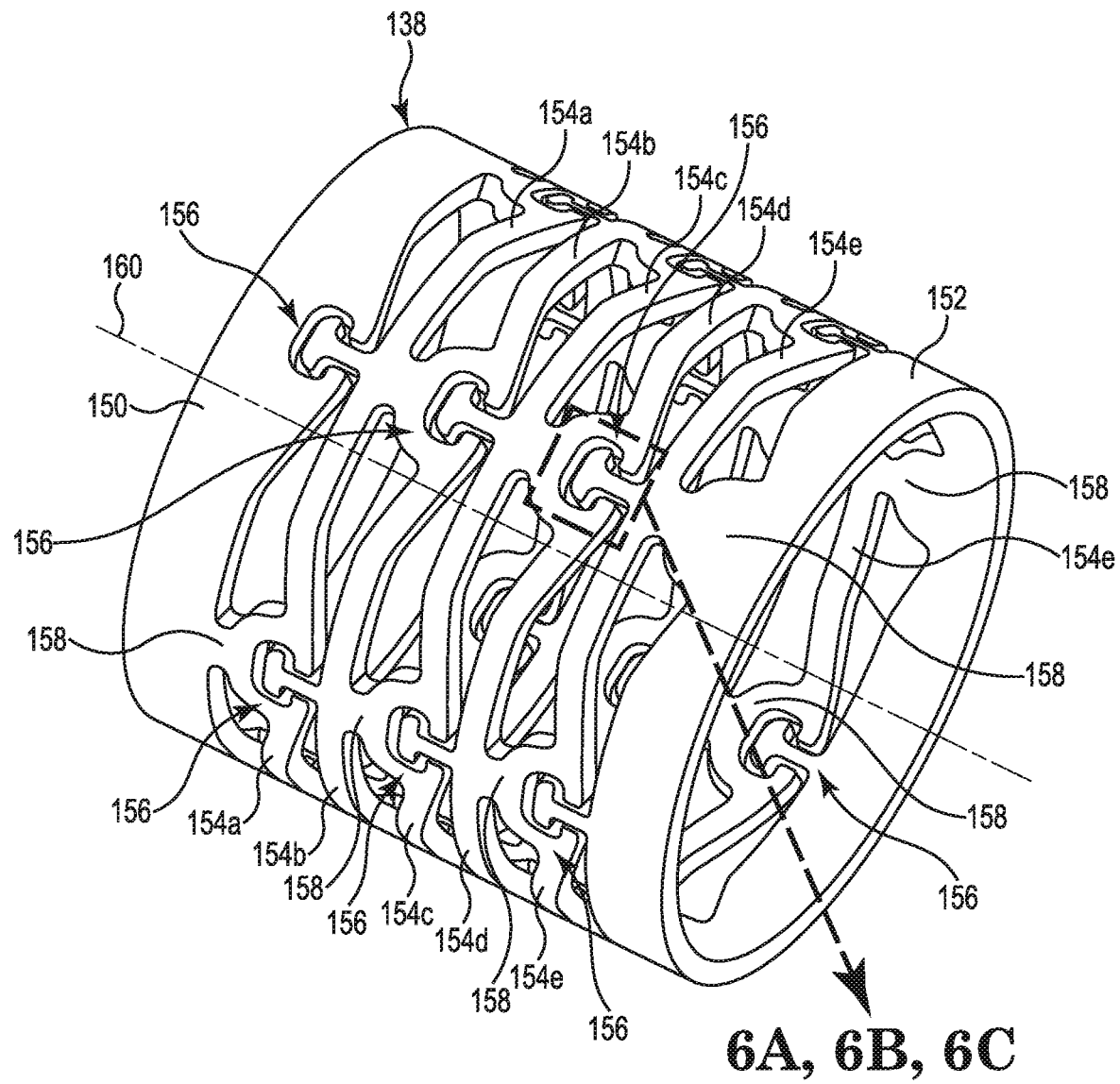
FIG. 5 is a perspective view of a spring element of FIG. 4 in accordance with various embodiments of this disclosure.

FIG. 5 shows a perspective view of the spring element 138 of FIG. 4, in accordance with embodiments of this disclosure. As shown in FIG. 5, the spring element 138 includes a first ring 150, a second ring 152, a plurality of struts 154, and a plurality of interlocking features 156. In the embodiment of FIG. 5, the plurality of struts 154 are interconnected to each other and to the first ring 150 and the second ring 152 by a plurality of interconnects 158 to connect the first ring 150 to the second ring 152.

As noted above and shown in FIG. 5, the spring element 138 is a tubular structure and has a longitudinal axis 160 with the second ring 152 and the first ring 150 coaxially aligned with the longitudinal axis 160. In some embodiments, either of the first ring 150 or the second ring 152 can be attached to the proximal hub 134 and the other one of the first ring 150 or the second ring 152 can be attached to the distal hub 136 by welding or adhesive, as described above. So attached, the longitudinal axis 160 of the spring element 138 can be aligned with the longitudinal axis 109 of the distal end 116 of the catheter 110 in the base orientation (see e.g. FIGS. 1B and 4).

The plurality of struts 154 can extend at least partially in a circumferential direction with respect to the longitudinal axis 160. In the embodiment shown in FIG. 5, each of the plurality of struts 154 extends at least substantially in the circumferential direction. That is, a majority of the length of each of the plurality of struts 154 extends in the circumferential direction or, if angled from the circumferential direction, extends primarily in the circumferential direction. The plurality of interconnects 158 can extend in an axial direction between the first ring 150 and one of the plurality of struts 154 adjacent to the first ring 150, between the second ring 152 and one of the plurality of struts 154 adjacent to the second ring 152, and between any two of the plurality of struts 154 adjacent to each other. In the embodiment of FIG. 5, the plurality of struts 154 consists of five struts 154a, 154b, 154c, 154d, and 154e. The strut 154a is connected to the first ring 150 and the adjacent strut 154b. The strut 154e is connected to the second ring 152 and the adjacent strut 154d. The three remaining struts 154b, 154c, and 154d are each connected to two adjacent struts 154. Each of the five struts 154 is connected to the first ring 150, the second ring 152, and/or an adjacent strut 154 by three of the plurality of interconnects 158 spaced 120 degrees apart in a circumferential row on one axially facing side of the strut 154, and by another three of the plurality of interconnects 158 spaced 120 degrees apart in a circumferential row on an opposite axially facing side of the strut 154. The plurality of interconnects 158 on axially opposite sides of any of the plurality of struts 154 are spaced 60 degrees apart.

So configured, the plurality of struts 154 permit elastic, relative axial and radial displacement between the first ring 150 and the second ring 152 as spaces between the first ring 150 and the second ring 152 expand and contract as the spring element 138 flexes in response to the normal force from the tissue bending the distal end 116 (FIG. 4). The spaces are defined by, for example, the first ring 150 the strut 154a and any pair of circumferentially adjacent interconnects 158 connecting the first ring 150 to the strut 154a. In another example, the spaces are defined by the strut 154d, the adjacent strut 154e, and any pair of circumferentially adjacent interconnects 158 connecting the strut 154d to the strut 154e.

The plurality of locking features 156 can extend between the first ring 150 and one of the plurality of struts 154 adjacent to the first ring 150, between the second ring 152 and one of the plurality of struts 154 adjacent to the second ring 152, and between any two of the plurality of struts 154 adjacent to each other. For example, in FIG. 5, the plurality of locking features 156 can extend between the first ring 150 and the adjacent strut 154a, between the second ring 152 and the strut 154e, or between any of the struts 154b, 154c, or 154d and an adjacent strut 154. In the embodiment shown in FIG. 5, each of the plurality of interlocking features 156 is disposed at a circumferential midpoint between a pair of circumferentially adjacent interconnects 158. The plurality of interlocking features 156 do not interfere with the operation of the spring element 138 throughout an allowed range of tensile and compressive forces that elastically deform the spring element 138. The plurality of interlocking features 156 protects the spring element 138 from experiencing tensile and compressive forces that might otherwise be sufficient to plastically deform the spring element 138, as discussed below in reference to FIGS. 6A-6C.

In use, each of the plurality of struts 154 can experience axial compression when an axial force is applied to the end of the distal segment 113 (FIG. 4). Should a force with a large radial component, such as illustrated in FIG. 1C, be applied to the distal segment 113, some of the plurality of struts 154 farthest from the application of the force will experience a compressive force pushing the plurality of struts 154 toward each other, while those nearest the application of the force will experience a tensile force pulling the plurality of struts 154 apart from each other.

Figure 6A:
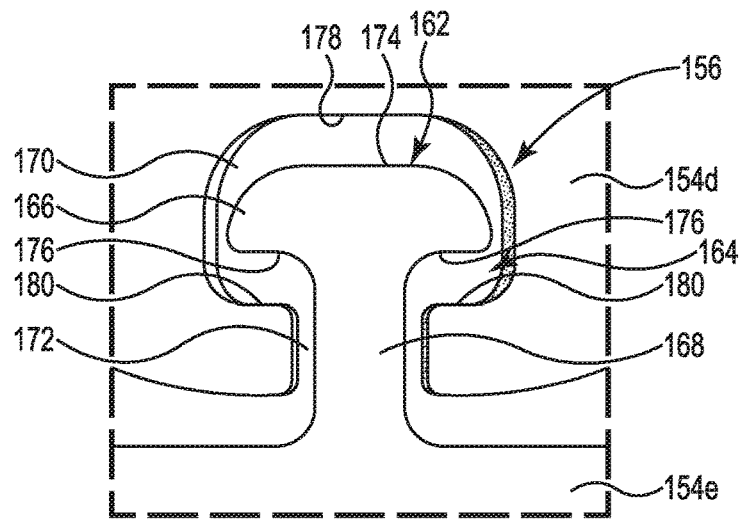
FIGS. 6A-6C are magnified views of an interlocking feature of the spring element of FIG. 5, in accordance with various embodiments of this disclosure.
Figure 6B:
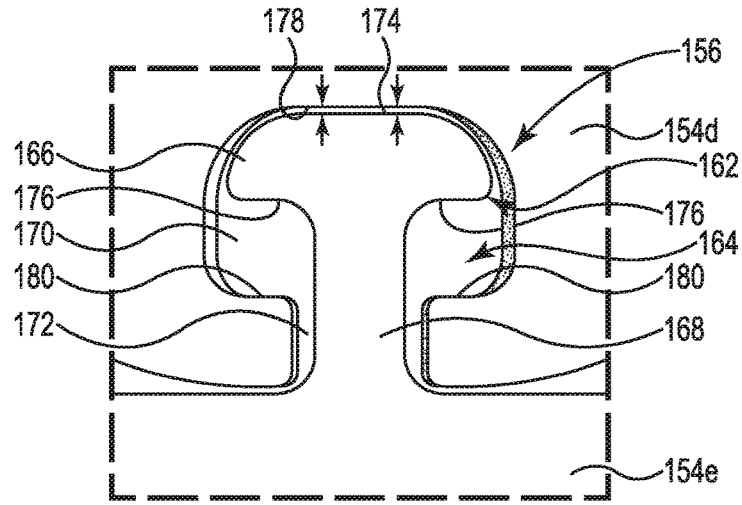
Figure 6C:
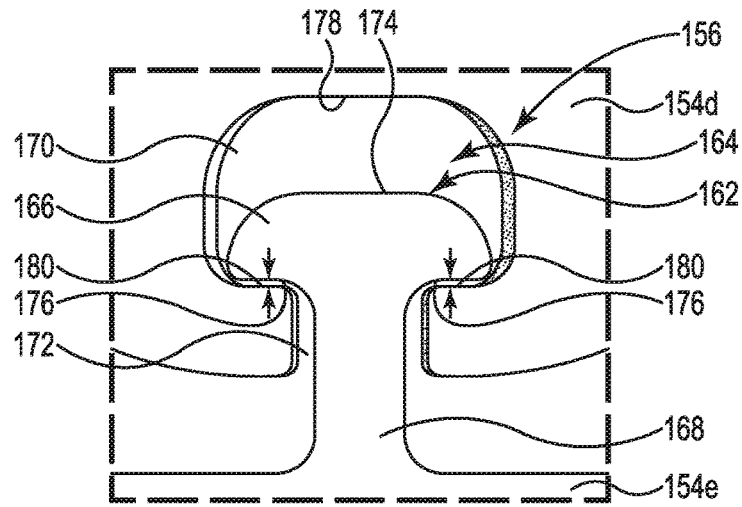

FIGS. 6A-6C show magnified views of one of the plurality of interlocking features 156 of the spring element 138 of FIG. 5, in accordance with embodiments of this disclosure. The interlocking feature 156 shown in FIGS. 6A-6C operates between the strut 154d and the strut 154e. FIG. 6A shows the interlocking feature 156 when the spring element 138 is not in axial compression or tension. As shown in FIG. 6A, the interlocking feature 156 can include a tab 162 extending from the strut 154e and an opening 164 defined by the strut 154d. The tab 162 can include a head portion 166 and a neck portion 168. The head portion 166 is wider in the circumferential direction than the neck portion 168. The opening 164 can included a wide region 170 and a narrow region 172. The narrow region 172 is narrower in the circumferential direction than the wide region 170. The wide region 170 is larger than the head portion 166 in that it is both wider in the circumferential direction and longer in the axial direction than the head portion 166. The narrow region 172 is wider in the circumferential direction than the neck portion 168, but narrower than the head portion 166. The head portion 166 is contained within the wide region 170 and the neck portion 168 extends through the narrow region 172.

The head portion 166 includes a first axially facing surface 174 facing away from the neck 168 and a second axial surface 176 facing a direction opposite the first axially facing surface 174. The wide region 170 includes a first edge 178 facing toward the first axially facing surface 174 and a second edge 180 facing the second axially facing surface 176. In use, over the allowed range of tensile and compressive forces that elastically deform the spring element 138, the tab 162 can freely move axially within the wide region 170, presenting no interference with the smooth and predictable displacement of the strut 154d relative to the strut 154e.

FIG. 6B shows the interlocking feature 156 when the spring element 138 is under a compressive stress that may exceed the allowed range of compressive forces and otherwise deform the spring element 138. As shown in FIG. 6B, the first axially facing surface 174 of the tab 166 physically contacts the first edge 178 of the wide region 170 so that the tab 170 can provide a physical support against the compression between the strut 154*d* and the strut 154*e*. The physical support at the midpoint be the pair of adjacent interconnects 158 (FIG. 5) in combination with the pair of adjacent interconnects 158 can significantly increase the amount of compressive force that the spring element 138 can withstand without plastically deforming the spring element 138.

FIG. 6C shows the interlocking feature 156 when the spring element 138 is under a tensile stress that may exceed the allowed range of tensile forces and otherwise deform the spring element 138. As shown in FIG. 6C, the second axially facing surface 176 of the tab 166 physically contacts the second edge 180 of the wide region 170 so that the tab 170 can limit the tensile motion of the strut 154*d* relative to the strut 154*e*. This ability to limit the tensile motion of the struts 154, such as strut 154*d* and 154*e*, protects the plurality of struts 154 which would otherwise be damaged by too much motion, significantly increasing the amount of tensile force that the spring element 138 can withstand without plastically deforming the spring element 138. Thus, the opening 164 is configured to engage the tab 162, as shown in FIGS. 6B and 6C.

Figure 7:
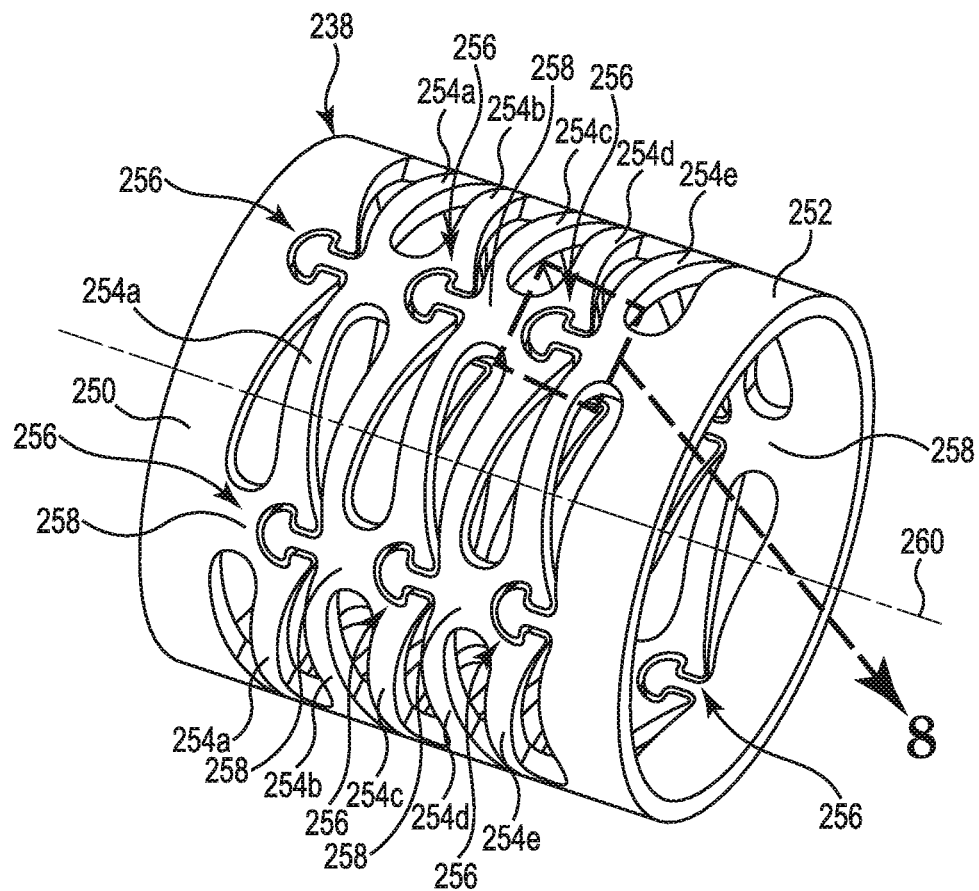
FIG. 7 is a perspective view of another embodiment of a spring element in accordance with various embodiments of this disclosure.

FIG. 7 is a perspective view of another embodiment of a spring element 238 in accordance with various embodiments of this disclosure. The spring element 238 can be used in the catheter 110 in the same way as the spring element 138 described above. The spring element 238 can be identical to the spring element 138 described above except as described below. As shown in FIG. 7, the spring element 238 includes a first ring 250, a second ring 252, a plurality of struts 254, and a plurality of interlocking features 256. In the embodiment of FIG. 7, the plurality of struts 254 are interconnected to each other and to the first ring 250 and the second ring 252 by a plurality of interconnects 258 to connect the first ring 250 to the second ring 252. As with the spring element 138, the spring element 238 is a tubular structure and has a longitudinal axis 260 with the second ring 252 and the first ring 250 coaxially aligned with the longitudinal axis 160.

The plurality of struts 254 can extend at least partially in a circumferential direction with respect to the longitudinal axis 260. In the embodiment shown in FIG. 7, each of the plurality of struts 254 extends at least substantially in the circumferential direction. That is, a majority of the length of each of the plurality of struts 254 extends in the circumferential direction or, if angled from the circumferential direction, extends primarily in the circumferential direction. In contrast to the spring element 138 shown in FIG. 5, the struts 254 of FIG. 7 have a more curvilinear shape which may improve the robustness of the spring element 238 by reducing peak stresses within the spring element 238 when subjected to tensile and compressive forces.

The plurality of interconnects 258 can extend in an axial direction between the first ring 250 and one of the plurality of struts 254 adjacent to the first ring 250, between the second ring 252 and one of the plurality of struts 254 adjacent to the second ring 252, and between any two of the plurality of struts 254 adjacent to each other. In the embodiment of FIG. 7, the plurality of struts 254 consists of five struts 254*a*, 254*b*, 254*c*, 254*d*, and 254*e*. The strut 254*a* is connected to the first ring 250 and the adjacent strut 254*b*. The strut 254*e* is connected to the second ring 252 and the adjacent strut 254*d*. The three remaining struts 254*b*, 254*c*, and 254*d* are each connected to two adjacent struts 254. Each of the five struts 254 is connected to the first ring 250, the second ring 252, and/or an adjacent strut 254 by three of the plurality of interconnects 258 spaced 120 degrees apart in a circumferential row on one axially facing side of the strut 254, and by another three of the plurality of interconnects 258 spaced 120 degrees apart in a circumferential row on an opposite axially facing side of the strut 254. The plurality of interconnects 258 on axially opposite sides of any of the plurality of struts 254 are spaced 60 degrees apart.

So configured, the plurality of struts 254 permit elastic, relative axial and radial displacement between the first ring 250 and the second ring 252 as spaces between the first ring 250 and the second ring 252 expand and contract as the spring element 238 flexes in response to the normal force from the tissue bending the distal end 116 (FIG. 4). The spaces are defined by, for example, the first ring 250 the strut 254*a* and any pair of circumferentially adjacent interconnects 258 connecting the first ring 250 to the strut 254*a*. In another example, the spaces are defined by the strut 254*d*, the adjacent strut 254*e*, and any pair of circumferentially adjacent interconnects 258 connecting the strut 254*d* to the strut 254*e*.

The plurality of locking features 256 can extend between the first ring 250 and one of the plurality of struts 254 adjacent to the first ring 250, between the second ring 252 and one of the plurality of struts 254 adjacent to the second ring 252, and between any two of the plurality of struts 254 adjacent to each other. For example, in FIG. 7, the plurality of locking features 256 can extend between the first ring 250 and the adjacent strut 254*a*, between the second ring 252 and the strut 254*e*, or between any of the struts 254*b*, 254*c*, or 254*d* and an adjacent strut 254. In the embodiment shown in FIG. 7, each of the plurality of interlocking features 256 is disposed at a circumferential midpoint between a pair of circumferentially adjacent interconnects 258. The plurality of interlocking features 256 do not interfere with the operation of the spring element 238 throughout an allowed range of tensile and compressive forces that elastically deform the spring element 238. The plurality of interlocking features 256 protects the spring element 238 from experiencing tensile and compressive forces that might otherwise be sufficient to plastically deform the spring element 238, as discussed above for the locking feature 156 in reference to FIGS. 6A-6C.

Figure 8:
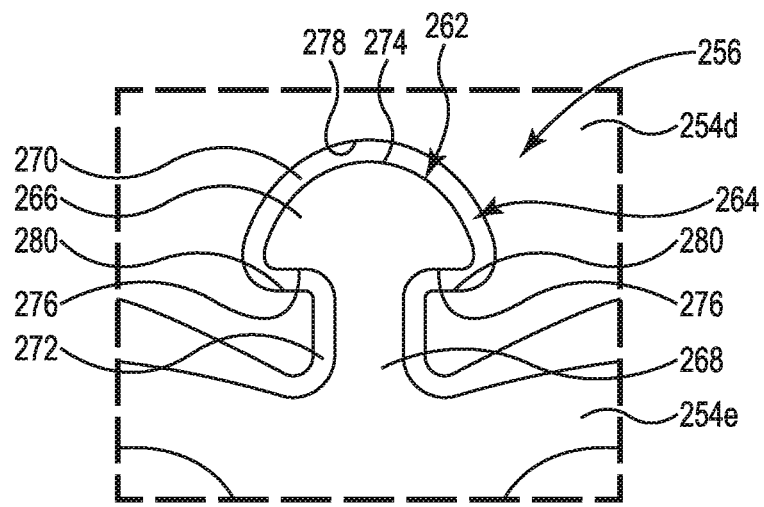
FIG. 8 is a magnified view of an interlocking feature of the spring element of FIG. 7, in accordance with various embodiments of this disclosure.

In contrast to the plurality of locking features 156 shown in FIGS. 5 and 6A-6C, the locking feature 256 shown in FIG. 7 is has more of a curvilinear shape. FIG. 8 is a magnified view of the interlocking feature 256 of the spring element 238 of FIG. 7, in accordance with various embodiments of this disclosure. As shown in FIG. 8, the interlocking feature 256 can include a tab 262 extending from the strut 254*e* and an opening 264 defined by the strut 254*d*. The tab 262 can include a head portion 266 and a neck portion 268. The head portion 266 is wider in the circumferential direction than the neck portion 268. The opening 264 includes a wide region 270 and a narrow region 272. The narrow region 272 is narrower in the circumferential direction than the wide region 270. The wide region 270 is larger than the head portion 266 in that it is both wider in the circumferential direction and longer in the axial direction than the head portion 266. The narrow region 272 is wider in the circumferential direction than the neck portion 268, but narrower than the head portion 266. The head portion 266 is contained within the wide region 270 and the neck portion 268 extends through the narrow region 272.

The head portion 266 includes a first axially facing surface 274 facing away from the neck 268 and a second axial surface 276 facing a direction opposite the first axially facing surface 274. The wide region 270 includes a first edge 278 facing toward the first axially facing surface 274 and a second edge 280 facing the second axially facing surface 276. The first axially facing surface 274 can be a curved surface when viewed radially, as shown in FIG. 8, in contrast to the largely flat surface of the first axially facing surface 174 as shown in FIG. 6A. Similarly, the first edge 278 can be a curved surface when viewed radially, as shown in FIG. 8, in contrast the largely flat surface of the first edge 178 as shown in FIG. 6A. In use, over the allowed range of tensile and compressive forces that elastically deform the spring element 238, the tab 262 can freely move axially within the wide region 270, presenting no interference with the smooth and predictable displacement of the strut 254d relative to the strut 254e. The locking feature 256 also protects the plurality of struts 254 as described above in reference to FIGS. 6B and 6C for the plurality of struts 154 including the ability to limit the tensile motion of the plurality of struts 254 which would otherwise be damaged by too much motion, significantly increasing the amount of tensile force that the spring element 238 can withstand without plastically deforming the spring element 238.

Figure 9:
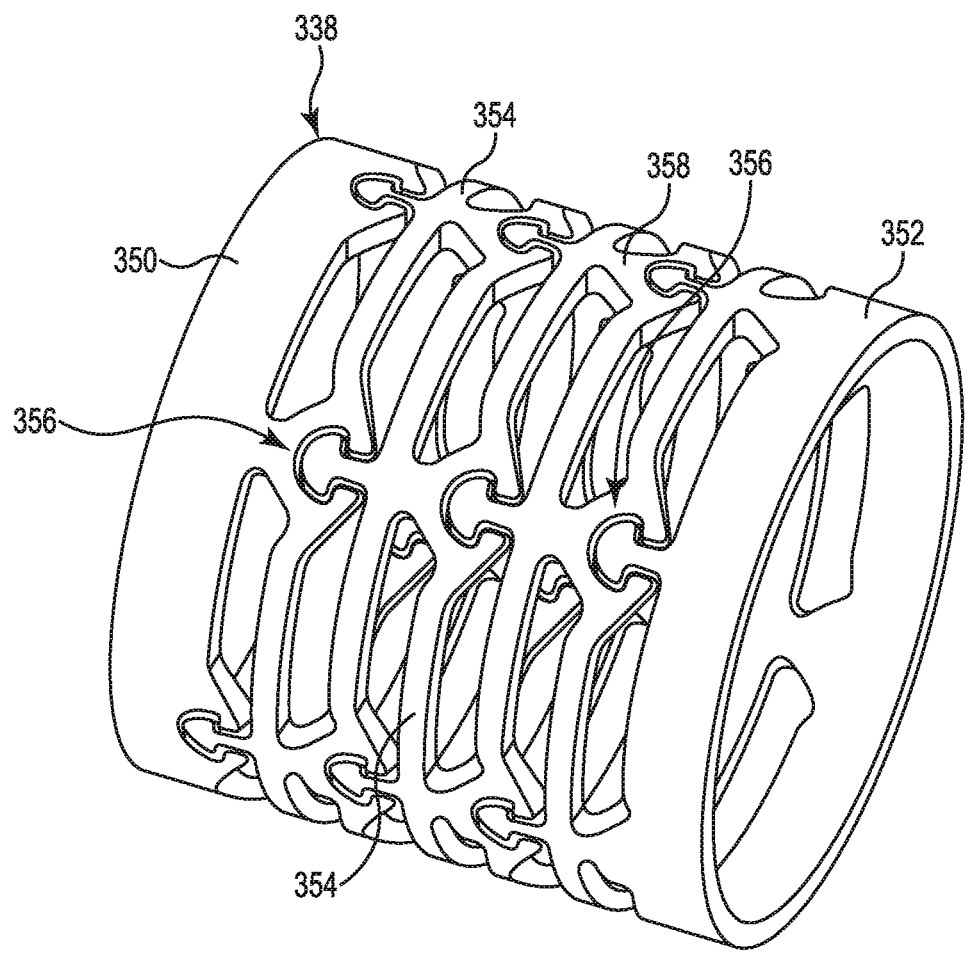
FIG. 9 is a perspective view of another embodiment of a spring element in accordance with various embodiments of this disclosure.

FIG. 9 is a perspective view of another embodiment of a spring element 338 in accordance with various embodiments of this disclosure. The spring element 338 can be used in the catheter 110 in the same way as the spring elements 138 and 238 described above. As shown in FIG. 9, the spring element 338 includes a first ring 350, a second ring 352, a plurality of struts 354, and a plurality of interlocking features 356. In the embodiment of FIG. 9, the plurality of struts 354 are interconnected to each other and to the first ring 350 and the second ring 352 by a plurality of interconnects 358 to connect the first ring 350 to the second ring 352. The plurality of struts 354 is similar to the plurality of struts 154 of the spring element 138. The plurality of interlocking features 356 is similar to the plurality of locking features 256 of the spring element 238. Thus, the spring element 338 incorporates features of both the spring element 138 and the spring element 238. Other embodiments may include different combinations of features, for example, the plurality of struts 254 of the spring element 238 with the plurality of locking features 156 of the spring element 238.

For ease of illustration, the embodiments shown in FIG. 5-9, included the same arrangement and number of struts (154, 254, 354) and interlocking features (156, 256, 356). However, it is understood that embodiments can include spring elements having greater or fewer numbers of struts (154, 254, 354) and/or locking features (156, 256, or 356). For example, the spring element 154, the plurality of locking features 156 are in six axially aligned rows 60 degrees apart. This symmetrical arrangement of a factor of three can allow for more efficient calculation by the control unit 120 of the force vectors as sensed by the three sensing elements 140. In other embodiments, different numbers and arrangements can be employed, even though the force vector calculations may not be as efficient. In addition, it is understood that embodiments can include spring elements employing a mixture of interlocking features, for example, some interlocking features 156 and some interlocking features 256.

Figure 10:
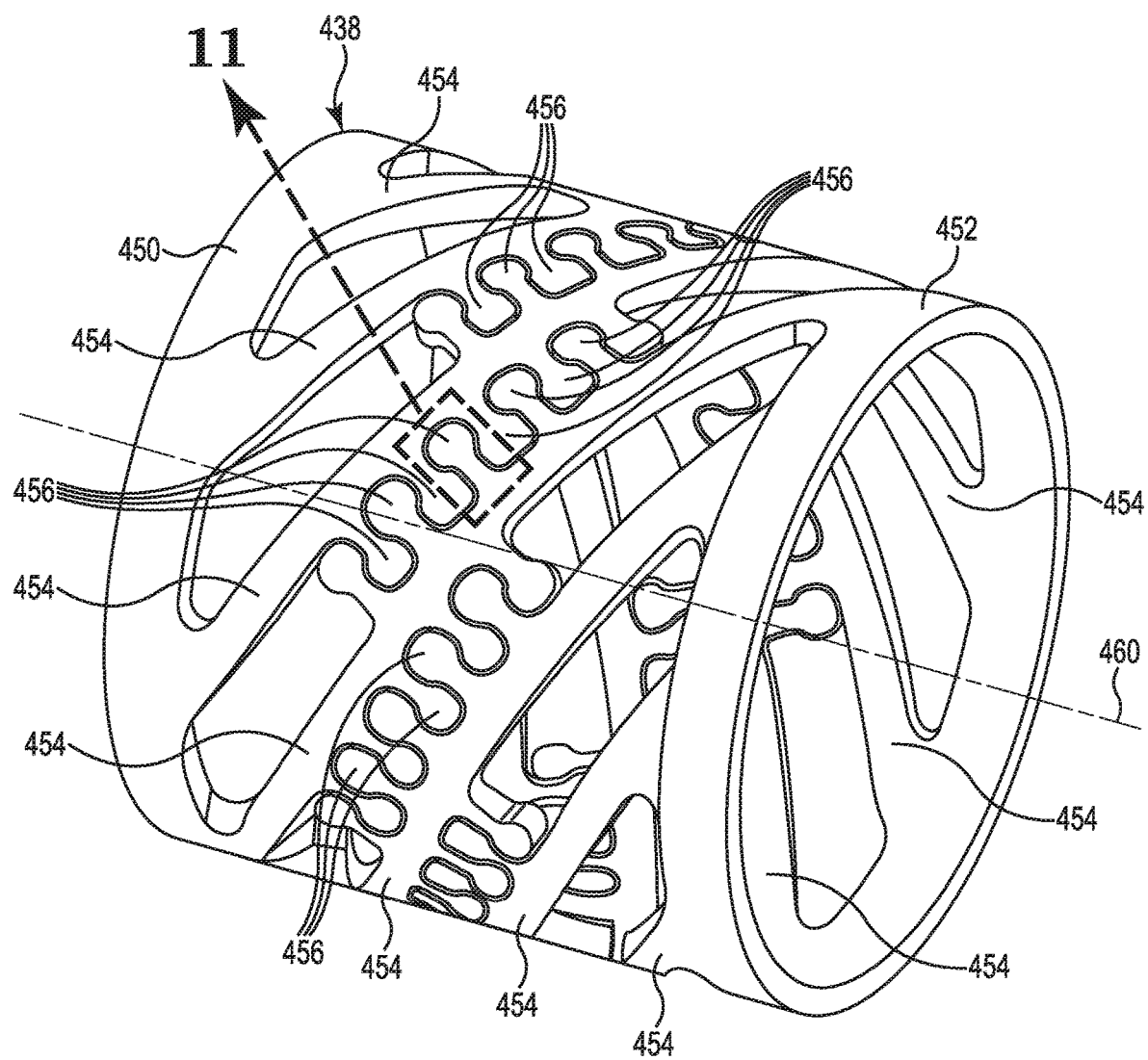
FIG. 10 is a perspective view of another embodiment of a spring element in accordance with various embodiments of this disclosure.

FIG. 10 is a perspective view of another embodiment of a spring element 438 in accordance with various embodiments of this disclosure. The spring element 438 can be used in the catheter 110 in the same way as the spring elements 138, 238, and 338 described above. As shown in FIG. 10, the spring element 438 includes a first ring 450, a second ring 452, a plurality of struts 454, and a plurality of interlocking features 456. In the embodiment of FIG. 10, each of the plurality of struts 454 extends directly between the first ring 450 and the second ring 452 to connect the first ring 450 to the second ring 452.

The spring element 438 is a tubular structure and has a longitudinal axis 460 with the second ring 452 and the first ring 450 coaxially aligned with the longitudinal axis 460. Each of the plurality of struts 454 runs diagonally between the first ring 450 and the second ring 452. That is, each of the plurality of struts 454 extends in both the circumferential direction and in the axial direction. In the embodiment shown in FIG. 10, each of the plurality of struts 454 extends primarily in the circumferential direction. In other embodiments, each of the plurality of struts 454 may extend primarily in the axial direction or in the circumferential and radial directions equally. As shown in FIG. 10, the plurality of struts 454 includes eight struts 454. So configured, the plurality of struts 454 permit elastic, relative axial and radial displacement between the first ring 450 and the second ring 452 as spaces between the first ring 450 and the second ring 452 expand and contract as the spring element 438 flexes in response to the normal force from the tissue bending the distal end 116 (FIG. 4). The spaces are defined by the first ring 450, the second ring 452 and any two of the plurality of struts 454 adjacent to each other. The first ring 450 and the second ring 452 will be displaced about the longitudinal axis 460 relative to each other as the spaces between the first ring 450 and the second ring 452 expand and contract.

The plurality of locking features 456 can extend between any two of the plurality of struts 454 adjacent to each other. In the embodiment shown in FIG. 10, the plurality of locking features 456 extend between each pair of adjacent struts 454. The plurality of interlocking features 456 do not interfere with the operation of the spring element 438 throughout an allowed range of tensile and compressive forces that elastically deform the spring element 438. The plurality of interlocking features 456 protects the spring element 438 from experiencing tensile and compressive forces that might otherwise be sufficient to plastically deform the spring element 438. In addition, the plurality of locking features 456 can limit the amount of rotational displacement between the first ring 450 and the second ring 452.

Figure 11:
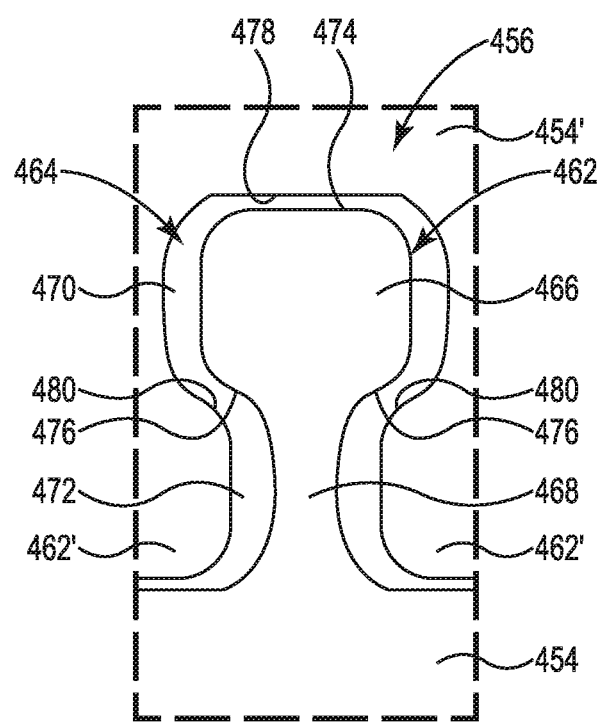
FIG. 11 is a magnified view of an interlocking feature of the spring element of FIG. 10, in accordance with various embodiments of this disclosure.

FIG. 11 is a magnified view of one of the plurality of interlocking features 456 of the spring element 438 of FIG. 10, in accordance with various embodiments of this disclosure. As shown in FIG. 11, the interlocking feature 456 can include a tab 462 extending from one of the plurality of struts 454 and an opening 464 defined by an adjacent one of the plurality of struts 454, designated 454'. The tab 462 can include a head portion 466 and a neck portion 468. The head portion 466 is wider in the than the neck portion 468. The opening 464 includes a wide region 470 and a narrow region 472. The narrow region 472 is narrower than the wide region 470. The wide region 470 is larger than the head portion 466. The narrow region 472 is wider than the neck portion 468, but narrower than the head portion 466. The head portion 466 is contained within the wide region 470 and the neck portion 468 extends through the narrow region 472.

A pair of tabs 462, designated 462', extending from the adjacent strut 454' can define the opening 464 for the tab 462 extending from the strut 454. In this way, several interlocking features 456 can be disposed near the midpoints of each of the plurality of struts 454 (see FIG. 10).

The head portion 466 includes a first surface 274 facing away from the neck 468 and a second surface 476 facing a direction opposite the first surface 474. The wide region 470 includes a first edge 478 facing toward the first surface 474 and a second edge 480 facing the second surface 476.

In use, over the allowed range of tensile and compressive forces that elastically deform the spring element 438, the tab 462 can freely move axially within the wide region 470, presenting no interference with the smooth and predictable displacement of the strut 454 relative to the adjacent strut 454'. The locking feature 456 also protects the plurality of struts 454 as described above in reference to FIGS. 6B and 6C for the plurality of struts 154 including the ability to limit the tensile motion of the plurality of struts 454 which would otherwise be damaged by too much motion, significantly increasing the amount of tensile force that the spring element 438 can withstand without plastically deforming the spring element 438.

Figure 12:
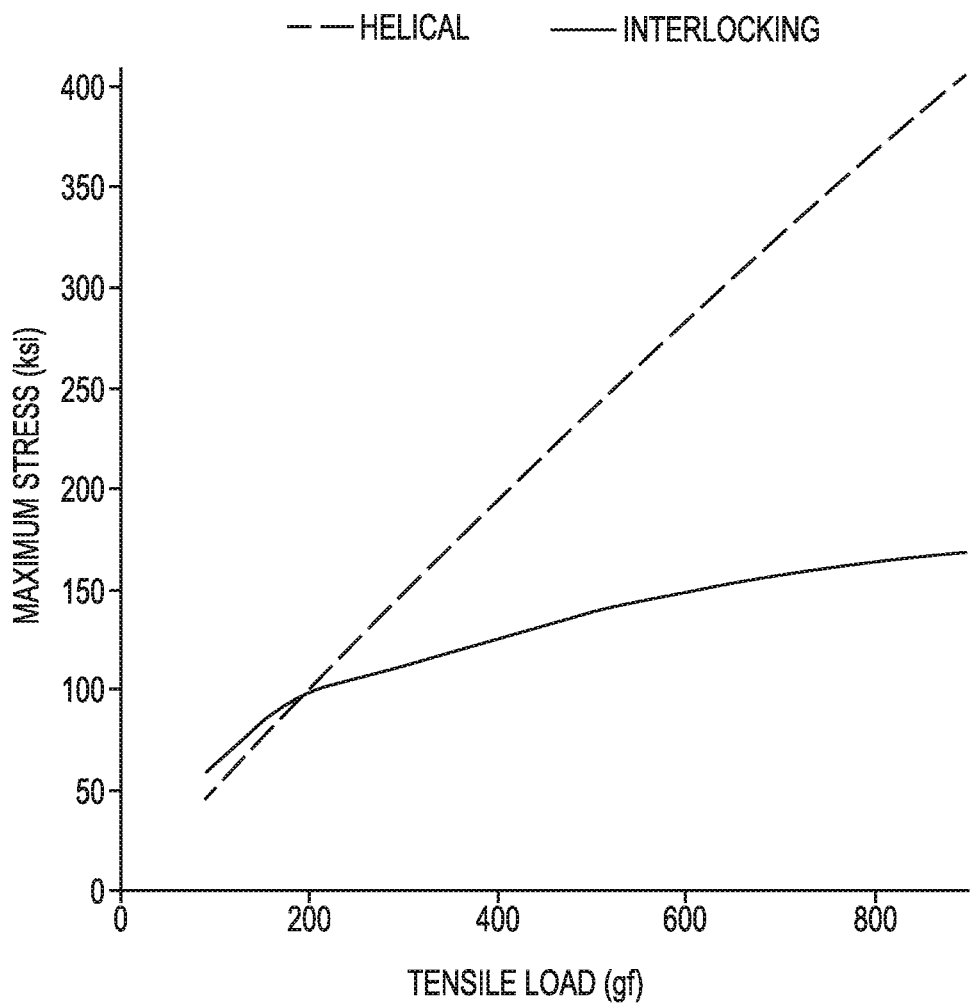
FIG. 12 is a graph comparing the predicted performance of a prior art helical spring element to a spring element in accordance with various embodiments of this disclosure.

FIG. 12 is a graph comparing the performance of a helical spring element that does not include interlocking features (HELICAL) to a spring element including a plurality of interlocking features according to embodiments of this disclosure (INTERLOCKING). The data presented in FIG. 12 is based on predictive models. FIG. 12 shows a maximum calculated stress in units of kilopounds per square inch (ksi) over a range of applied tensile loads in units of gram-force (gf). As shown in FIG. 12, the spring element including the interlocking features should experience a significantly lower maximum stress compared to the helical spring element over a wide range of applied tensile loads. Such tensile loads could occur, for example, when withdrawing the catheter through a hemostatic seal. As the interlocking features engage, they would prevent the spring element from being overstressed and suffering plastic deformation, which could otherwise occur at about 200 ksi. The helical spring element without the interlocking features would exceed the yield limit of 200 ksi and could plastically deform because it does not have such protection. By limiting the maximum stress experienced by the spring element, the locking features can protect the spring element from plastic deformation which would otherwise change the calibration of the catheter such that force sensing measurements from the catheter may no longer be accurate.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A spring element for a contact force sensing medical catheter, the spring element comprising:
   a first ring;
   a second ring spaced apart from the first ring, the second ring and the first ring coaxially aligned with a longitudinal axis of the spring element; and
   a plurality of struts connecting the first ring to the second ring, each of the plurality of struts connected to an adjacent strut by an interconnect configured to define a space between adjacent struts, the plurality of struts configured to elastically deform so as to permit relative axial and radial displacement between the first ring and the second ring;
   wherein each of the plurality of struts includes a plurality of interlocking features configured to limit the relative axial and radial displacement between the first ring and the second ring, each of the plurality of interlocking features interlocking with an adjacent strut of the plurality of struts, wherein at least some of the interlocking features include a head portion and a neck portion, the head portion having a first axially facing surface facing away from the neck portion and a second axially facing surface facing a direction opposite the first surface, wherein the first surface and the second surface are substantially parallel to one another.

2. The spring element of claim 1, wherein each of the plurality of struts extends at least partially in a circumferential direction to permit elastic relative axial and radial displacement between the first ring and the second ring.

3. The spring element of claim 2, wherein each of the plurality of struts extends at least substantially in the circumferential direction and the plurality of struts are interconnected.

4. The spring element of claim 2, wherein each of the plurality of struts extends directly between the first ring and the second ring and in both the circumferential direction and an axial direction.

5. The spring element of claim 1, wherein each of the interlocking features extends between the first ring and one of the plurality of struts adjacent to the first ring, between the second ring and one of the plurality of struts adjacent to the second ring, or between two of the plurality of struts adjacent to each other.

6. The spring element of claim 5, wherein each of the interlocking features includes:
   a tab extending from one of the first ring, the second ring, or the one of the plurality of struts; and
   an opening defined in one of the first ring, the second ring, or another one of the plurality of struts adjacent to the one of the first ring, the second ring, or the one of the plurality of struts from which the tab extends, the opening configured to engage the tab.

7. The spring element of claim 6, wherein for at least some of the interlocking features:
   the tab includes the head portion and the neck portion connecting the head portion to the one of the first ring, the second ring, or the one of the plurality of struts, the head portion being wider than the neck portion; and
   the opening includes a wide region and a narrow region, wherein the wide region is larger wider in a circumferential direction and longer in an axial direction than the head portion of the tab, the narrow region is wider than the neck portion of the tab, and the narrow region is narrower than the head portion of the tab, the head portion of the tab contained within the wide region and the neck portion of the tab extending through the narrow region such that the opening engages the tab to limit the relative axial and radial displacement between the first ring and the second ring.

8. A spring element for a contact force sensing medical catheter, the spring element comprising:
   a first ring;
   a second ring spaced apart from the first ring, the second ring and the first ring coaxially aligned with a longitudinal axis of the spring element;
   a plurality of struts configured to elastically deform to moveably couple the first ring to the second ring, each of the plurality of struts connected to an adjacent strut by an interconnect configured to define a space between adjacent struts; and
   wherein the plurality of struts includes a plurality of interlocking features configured to limit the relative axial and radial displacement between the first ring and the second ring, each of the interlocking features formed in the first ring and engaging one of the plurality of struts adjacent to the first ring, formed in one of the plurality of struts adjacent to the second ring and engaging the second ring, or formed in one of the plurality of struts and engaging a strut adjacent to the one of the plurality of struts, each of the interlocking features including:
- a tab including a head portion and a neck portion extending from one of the first ring or the one of the plurality of struts; and
- an opening defined in one of the second ring, or another one of the plurality of struts adjacent to the one of the first ring or the one of the plurality of struts from which the tab extends, the opening configured to engage the tab, the opening including a wide region and a narrow region, wherein the wide region contains the head portion and is wider in a circumferential direction and longer in an axial direction than the head portion, wherein the narrow region is wider than the neck portion of the tab, the narrow region is narrower than the head portion of the tab, and wherein the narrow region is defined by two opposing surfaces substantially parallel to the neck portion.

9. A catheter adapted to measure a contact force, the catheter comprising:
- a proximal segment;
- a distal segment;
- a spring segment extending from the proximal segment to the distal segment, the spring segment configured to permit relative displacement between the distal segment and the proximal segment in response to an application of the force on the distal segment, the spring segment including:
  - a spring element including:
    - a first ring;
    - a second ring spaced apart from the first ring, the second ring and the first ring coaxially aligned with a longitudinal axis of the spring element; and
    - a plurality of struts configured to elastically deform, the plurality of struts elastically coupling the first ring to the second ring and configured to permit elastic, relative axial and radial displacement between the first ring and the second ring;
  - wherein the plurality of struts includes a plurality of interlocking features configured to limit the relative axial and radial displacement between the first ring and the second ring, wherein each of the plurality of interlocking features is formed in a strut of the plurality of struts and interlocks with an adjacent strut of the plurality of struts;
  - wherein the plurality of interlocking features includes:
    - a tab including a head portion and a neck portion connecting the head portion to one of the first ring, the second ring, or one of the plurality of struts, the head portion being wider than the neck portion; and
    - an opening including a wide region and a narrow region, wherein the wide region is wider in a circumferential direction and longer in an axial direction than the head portion, wherein the narrow region is wider than the neck portion of the tab, the narrow region is narrower than the head portion of the tab, and wherein the narrow region is defined by two opposing surfaces substantially parallel to the neck portion, the head portion of the tab contained within the wide region and the neck portion of the tab extending through the narrow region such that the opening engages the tab to limit the relative axial and radial displacement between the first ring and the second ring; and
  - a plurality of sensing elements configured to output a plurality of signals indicative of the relative displacement between the proximal segment and the distal segment.

10. The catheter of claim 9, wherein each of the plurality of struts extends at least partially in a circumferential direction to permit elastic relative axial and radial displacement between the first ring and the second ring, and the plurality of struts are interconnected.

11. The catheter of claim 9, wherein the each of the interlocking features extends between the first ring and one of the plurality of struts adjacent to the first ring, between the second ring and one of the plurality of struts adjacent to the second ring, or between two of the plurality of struts adjacent to each other.

12. The catheter of claim 11, wherein each of the interlocking features includes:
- the tab extending from one of the first ring, the second ring, or the one of the plurality of struts; and
- the opening is defined in one of the first ring, the second ring, or another one of the plurality of struts adjacent to the one of the first ring, the second ring, or the one of the plurality of struts from which the tab extends, the opening configured to engage the tab.

13. The catheter of claim 9, wherein the spring element is a one-piece spring element.

14. The catheter of claim 9, wherein the plurality of sensing elements include a plurality of inductive sensors configured to signal a change in inductance caused by changes in the relative displacement between the proximal segment and the distal segment.

15. The catheter of claim 9, wherein:
the proximal segment includes a proximal hub; and
the distal segment includes a distal hub,
wherein the first ring of the spring element is attached to the proximal hub and the second ring of the spring element is attached to the distal hub.

16. The catheter of claim 15, wherein:
when the distal segment is in a base orientation with respect to the proximal segment, the proximal and distal hubs are coaxially aligned with the longitudinal axis of the spring element; and
when the distal segment is moved out of the base orientation with respect to the proximal segment, the distal hub is no longer coaxially aligned with the longitudinal axis of the spring element.

17. The catheter of claim 9, wherein the distal segment includes an ablation element configured to deliver ablation therapy.

18. The catheter of claim 9, wherein the distal segment includes a distal hub, and the plurality of sensing elements include a rod connected to the distal hub.

* * * * *